United States Patent [19]

Bergfeld et al.

[11] Patent Number: 5,124,450
[45] Date of Patent: Jun. 23, 1992

[54] PROCESS FOR THE PREPARATION OF 2-AMINODITHIOTHIAZOLES AND 2-AMINOTRITHIOTHIAZOLES

[75] Inventors: Manfred J. Bergfeld, Erlenbach; Ludwig Eisenhuth, Obernburg, both of Fed. Rep. of Germany

[73] Assignee: Akzo N.V., Netherlands

[21] Appl. No.: 775,504

[22] Filed: Oct. 15, 1991

[30] Foreign Application Priority Data

Oct. 15, 1990 [DE] Fed. Rep. of Germany ....... 4032680

[51] Int. Cl.$^5$ ............................................ C07D 417/12
[52] U.S. Cl. ................................... 544/136; 540/603; 544/368; 546/198
[58] Field of Search ............... 540/603; 544/136, 368; 546/198

[56] References Cited

U.S. PATENT DOCUMENTS

| | | | |
|---|---|---|---|
| 2,983,726 | 5/1961 | Hendry | 548/136 |
| 3,281,418 | 10/1966 | Budd et al. | 548/136 |
| 3,489,754 | 1/1970 | D'Amico | 544/136 |
| 3,969,350 | 7/1976 | D'Amico et al. | 548/136 |
| 4,182,873 | 1/1980 | Janin | 544/136 |

Primary Examiner—Robert W. Ramsuer
Attorney, Agent, or Firm—Oliff & Berridge

[57] ABSTRACT

2-(aminodithio)thiazoles and 2-(aminotrithio)thiazoles are prepared by reacting a mixture of a 2-mercaptothiazole or a dithiazolyl 2,2'-disulphide with a saturated secondary heterocyclic amine and sulphur in a reaction medium containing an inert organic solvent in the presence of an oxidant. The reaction is carried out in the present of ammonia and a catalyst containing copper, a copper compound or a cerium compound, and the oxidant is molecular oxygen or a gas containing oxygen. In particular, 2-(4-morpholinodithio)benzo-thiazole, which is technically interesting as a vulcanization accelerator, can be prepared in high product yield and virtually without by-products using the oxidant which is less expensive and can be handled with greater ease.

17 Claims, No Drawings

PROCESS FOR THE PREPARATION OF 2-AMINODITHIOTHIAZOLES AND 2-AMINOTRITHIOTHIAZOLES

BACKGROUND OF THE INVENTION

The present invention relates to a process for the preparation of 2-(aminodithio)thiazoles and 2-(aminotrithio)thiazoles by reacting a cyclic secondary amine, a 2-mercaptothiazole and sulphur in an inert organic solvent in the presence of an oxidant.

A typical representative of the compounds from the group of 2-aminodithiothiazoles is 2-(4-morpholinodithio)benzothiazole, which is used in large amounts as a vulcanization accelerator and sulphur donor. Processes for the preparation of 2-(4-morpholinodithio)benzothiazole have previously been described. They can be grouped as follows, depending on the starting compounds employed in each case: from morpholine sulphides and 2-mercaptobenzothiazole or dibenzothiazolyl 2,2'-disulphide (U.S. Pat. No. 3,489,754), from 2-mercaptobenzothiazole or dibenzothiazolyl 2,2'-disulphide, 4-morpholine and disulphur dichloride (U.S. Pat. No. 3,070,593), from 2-mercaptobenzothiazole, 4-morpholine, chlorine and disulphur dichloride (U.S. Pat. No. 2,983,726), from 2-mercaptobenzothiazole or dibenzothiazolyl 2,2'-disulphide, 4-morpholine, sulphur and oxidants such as sodium hypochlorite (DE-A 2,238,516), from morpholino-benzothiazole and sulphur (DE-A 1,134,677), and from sulphenamides, 4-morpholine and sulphur (U.S. Pat. No. 3,969,350). From amongst these, processes which are suitable for industrial realization are those which are based on the raw materials 2-mercaptobenzothiazole, 4-morpholine and sulphur, which are inexpensive and readily available, described in DE-A 2,238,516 and also in DE-A 2,164,480 and U.S. Pat. No. 3,281,418. According to the contents of these three publications, it is still necessary to employ expensive oxidants in a high stoichiometric excess, in particular those which are substantially soluble in water, in order to use them in aqueous solution. For example, ammonium peroxydisulphate or potassium peroxydisulphate, hydrogen peroxide, potassium permanganate and sodium hypochlorite or calcium hypochlorite are to be used, with sodium hypochlorite being preferred in all cases. The shortcoming encountered when most of these oxidants are used is that inorganic salts are formed as a by-product, for example sodium chloride in the case of the preferred sodium hydrochlorite, which contaminate the waste water or have to be removed. In these processes too, not only the oxidant but also the remaining reactants must be employed in high stoichiometric excesses.

A suggestion as to how the process for the preparation of 2-(4-morpholinodithio)benzothiazole from 2-mercaptobenzothiazole, 4-morpholine, sulphur and oxidant can be made more economical can be found in the above-mentioned publication DE-A 2,238,516. According to this publication, the 2-mercaptobenzothiazole is to be employed directly in the state in which it is obtained from the preparation of 2-mercaptobenzothiazole, i.e., water-moist and the drying step of the latter is thereby dispensed with.

SUMMARY OF THE INVENTION

An object of the present invention is to make the process for the preparation of 2-aminodithio-thiazoles from 2-mercaptothiazoles, secondary cyclic amines, sulphur and oxidants more economical and with less contamination of the waste water, namely by replacing the previously employed oxidants by a less expensive product which can be handled with greater ease.

This object is achieved by a process for the preparation of 2-(aminodithio)thiazoles and/or 2-(aminotrithio)thiazoles of the general formula (I)

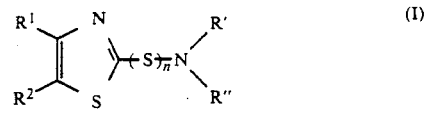

in which n is essentially 2 or 3, in which $R^1$ and $R^2$ can be identical or different and in each case represent a hydrogen atom, a halogen atom, a nitro group, a hydroxyl group, or represent an organic radical such as an alkyl or alkoxy radical having 1 to 6 carbon atoms or a cycloalkyl or aryl radical having 6 to 12 carbon atoms, which organic radical can optionally be monosubstituted or polysubstituted, the possible substituents in each case being a halogen atom, a nitro group, a hydroxyl group or an alkyl or alkoxy radical having 1 to 5 carbon atoms, or in which $R^1$ and $R^2$ together form the radical (II)

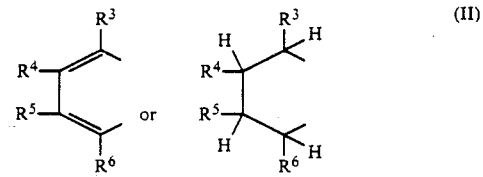

where $R^3$, $R^4$, $R^5$ and $R^6$ can be identical or different and in each case have the same meaning as $R^1$ and $R^2$, but do not form the radical (II), and in which $R^1$ and $R^2$ together with the amine nitrogen form an aliphatically saturated heterocyclic ring which can contain at least one further hetero atom, it being possible, if piperazine is the base of the heterocyclic ring, for the further nitrogen atoms also to carry the 2-thiazolyldithio or 2-thiazolyltrithio radical, by reacting a mixture of a 2-mercaptothiazole of the general formula (III) or dithiazolyl 2,2'-disulphide of the general formula (IV)

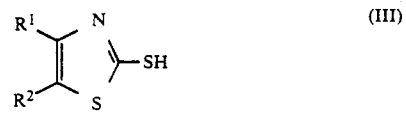

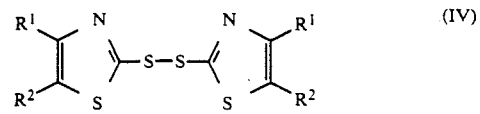

in which $R^1$ and $R^2$ have the above-mentioned meaning, a saturated secondary, heterocyclic amine of the general formula (V)

where R' and R" are as defined above, and sulphur, in a reaction medium containing an inert organic solvent, and in the presence of an oxidant, characterized in that the reaction is carried out in the presence of ammonia and a catalyst containing copper, a copper compound or a cerium compound, and in that the oxidant is molecular oxygen or a gas containing this oxygen The result which can be achieved with this new process can only be carried out using cyclic amines (V); not using a acyclic, aliphatic amines. Corresponding products with cyclic amines have previously not been known from the literature. On the other hand, by omitting the sulphur under process conditions which are, apart from this, according to the invention (i.e. reaction of only mercaptothiazole and cyclic amine in the presence of oxygen), only small amounts of cycloaminomonothiothiazole are obtained (see Experiment C2). This is surprising because of the contents of DE-A 3,325,724, which describes the preparation of aminomonothiothiazoles (designated as "sulphenamides" in this publication) from 2-mercaptobenzothiazole and amines in the presence of oxygen. De-A 3,325,724 allowed the assumption to be made that such a monothiothiazole was formed as an intermediate. Since this is not the case, it is evident that the mechanism of the reaction in the process according to the invention is a different one.

The substituents $R^1$ to $R^6$ of the general formulae I, II, III and IV are preferably a chlorine or bromine atom, a hydroxyl group, a nitro group, a straight-chain or branched alkyl radical 1-4 carbon atoms such as a methyl, ethyl, propyl, isopropyl, butyl or tert-butyl radical, an alkoxy radical having 1-4 carbon atoms such as a methoxy, ethoxy, propoxy or butoxy radical or a phenyl, tolyl, ethylphenyl, nitrophenyl, chlorophenyl, bromophenyl or naphthyl radical.

DETAILED DESCRIPTION OF PREFERRED EMBODIMENTS

The process according to the invention is particularly suitable for the preparation of 2-(aminodithio)-thiazoles and 2-(aminotrithio)thiazoles from 2-mercaptobenzothiazole or dithiazolyl 2,2'-disulphide, the most important representatives of the 2-mercaptobenzothiazoles or dibenzothiazolyl 2,2'-disulphides. Examples of other 2-mercaptothiazoles which are suitable as starting compounds for the preparation according to the invention of 2-aminodithiothiazoles of the general formula (I) are the following compounds:
2-mercaptothiazole
2-mercapto-4-methylthiazole
2-mercapto-4-ethylthiazole
2-mercapto-4-n-propylthiazole
2-mercapto-4-n-butylthiazole
2-mercapto-4,5-dimethylthiazole
2-mercapto-4,5-diethylthiazole
2-mercapto-4,5-di-n-propylthiazole
2-mercapto-4,5-di-n-butylthiazole
2-mercapto-phenylthiazole
2-mercapto-4-phenyl-5-methylthiazole
2-mercapto-4-phenyl-5-chlorothiazole
2-mercapto-4-m-chlorophenylthiazole
2-mercapto-4-p-bromophenylthiazole
2-mercapto-4-m-nitrophenylthiazole
2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-6-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole
2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole
2-mercapto-5-chloro-6-methoxybenzothiazole
2-mercapto-5-chloro-4-nitrobenzothiazole
2-mercapto-5-chloro-6-nitrobenzothiazole
2-mercapto-4,5-dichlorobenzothiazole
2-mercapto-4,7-dichlorobenzothiazole
2-mercapto-5-nitrobenzothiazole
2-mercapto-6-nitrobenzothiazole
2-mercapto-6-hydroxybenzothiazole
2-mercapto-tetrahydrobenzothiazole
2-mercapto-naphthothiazole Examples of other dithiazolyl 2,2'-disulphides as starting compounds in the process according to the invention are the following compounds:
bis-(6-methylbenzothiazolyl) 2,2'-disulphide
bis-(4-methylbenzothiazolyl) 2,2'-disulphide
bis-(4-methoxybenzothiazolyl) 2,2'-disulphide
bis-(6-ethoxybenzothiazolyl) 2,2'-disulphide
bis-(6-chlorobenzothiazolyl) 2,2'-disulphide
bis-(5-chloro-4-nitrobenzothiazolyl) 2,2'-disulphide
bis-(3-chloro-6-nitrobenzothiazolyl) 2,2'-disulphide
bis-(6-nitrobenzothiazolyl) 2,2'-disulphide
bis-(tetrahydrobenzothiazolyl) 2,2'-disulphide As starting compounds, dithiazolyl 2,2'-disulphides have an advantage over 2-mercaptothiazoles inasmuch as the chemical reaction proceeds substantially more rapidly (see Test Example 5) since only half the amount of oxygen is required in the reaction of the dithiazolyl 2,2'-disulphide as in the reaction of 2-mercaptothiazole.

According to the invention, the substituents R' and R" of the general formulae (I) and (V) together with the amine nitrogen form a saturated heterocyclic ring which can additionally contain at least one further hetero atom, hetero atom being understood as meaning, in particular, an oxygen, sulphur and nitrogen atom. That is to say that R' and R" form a polymethylene bridge or a polymethylene bridge with at least one methylene group which is replaced by, in particular, —O—, —S— and —NR— where R is H, $CH_3$, $C_2H_5$, $C_3H_7$, $C_4H_9$, $CH_2$—$CH_2$—OH. In the case of an —NH— group instead of a methylene group, that is to say when a piperazine is used a the starting compound, an N—N'-disubstituted compound, substituted by the 2-thiazolyldithio or the 2-thiazolyltrithio radical according to formula (I), can also be formed, provided that suitable stoichiometric amounts, i.e., twice the amounts of mercaptothiazole or thiazolyl 2,2'-disulphide are employed. The heterocyclic ring is preferably 5-, 6-or 7- membered and can have one or more, preferably one or two, inert substituents, for example alkyl groups having 1 to 4 carbon atoms, preferably methyl and ethyl groups, or alkylene groups, preferably a trimethylene or tetramethylene group, which form a further 5- or 6-membered ring with 2 adjacent carbon atoms of the heterocyclic ring.

Preferred secondary heterocyclic amines of the general formula (V) as starting compounds the process according to the invention are unsubstituted or substituted by alkyl groups having 1 to 4 carbon atoms, pyrrolidine, pyrazolidine, imidazolidine, oxazolidine, thiazolidine and, particularly preferably, piperidine, piperazine, cyclohexamethyleneimine and morpholine, in particular 4-morpholine. Examples of substituted secondary heterocyclic amines are 2- or 4-methylpiperidine, N-methylpiperazine, 2,6-dimethylmorpholine and 3,4-dimethylmorpholine.

In the process according to the invention, 2-mercaptothiazole or dithiazolyl 2,2'-disulphide, heterocyclic amine and sulphur can be used in stoichiometric amounts, or the starting compound (V) can be used in a slightly substoichiometric amount or in a stoichiometric excess of up to 100 mol% compared with the remaining starting compounds. It is preferred to employ 0.9 to 2 mol and particularly preferred to employ 0.9 to 1/5 mol of starting compound (V) per mole of 2-mercaptothiazole or equivalent of dithiaxolyl 2,2'-disulphide (starting compounds (III) and (IV) respectively). Depending on the reaction conditions and on the cyclic amine used, good results are obtained with a slight excess of amine of 0 to 0.1 mol. Of course, a higher stoichiometric excess of starting compound (V) can also be used, as is conventional, for example, in the prior art processes. According to the invention, a "stoichiometric excess" is understood as meaning the amount of the particular reactant which exceeds the amounts required for exact stoichiometric ratios.

As regards sulphur, two different types of stoichiometric amounts are to be used according to the invention: to prepare the dithiothiazoles, 1 equivalent of sulphur is required, and for the preparation of the trithiothiazoles 2 equivalents of sulphur are required per equivalent of 2-mercaptobenzothiazole or dithiazolyl 2,2'-disulphide; accordingly, amounts of sulphur in the range between 1 and 2 equivalents give mixtures of dithiazole and trithiazole. However, 3 equivalents of sulphur do not give a corresponding tetrathiazole compound; this only results in a mixture of trithiothiazole and sulphur.

The amount of the oxidant "molecular oxygen" or "gas containing molecular oxygen" is determined by the oxygen pressures or partial pressures. According to the invention, they are preferably not more than $10^6$ Pa superatmospheric pressure for economic and safety reasons, and not less than $10^4$ Pa. The reaction rate increases with increasing oxygen pressure.

The catalyst employed in the process according to the invention is metallic copper, a copper compound or a cerium compound, in each case in the presence of ammonia. Metallic copper is preferably employed in the form of copper powder. Suitable copper compounds are all monovalent or divalent inorganic, organic, simple or complex copper salts. Examples of suitable monovalent copper salts are copper(I) chloride, copper(I) bromide and copper(I) iodide, addition compounds of these copper(I) halides with carbon monoxide, complex copper(I) salts such as the alkali metal chlorocuprates, complex ammoniates of copper(I) cyanide, for example cyano-cuprates such as potassium tricyanocuprate(I), double salts with copper(I) thiocyanate, copper(I) acetate, copper(I) sulphite and complex double sulphides of copper(I) sulphide and alkali metal polysulphides. Examples of suitable copper(II) salts are copper(II) chloride, copper(II) bromide, copper(II) sulphide, copper(II) sulphate, copper(II) nitrate, copper(II) nitrite, copper(II) thiocyanate, copper(II) cyanide, Cu(II) salts of carboxylic acids such as copper(II) acetate, and the complex ammoniates of copper(II) salts. Copper(I) oxide is also very suitable as a catalyst. Suitable cerium compounds are all trivalent and tetravalent cerium compounds such as, for example, cerium(III) nitrate.

Preferred catalysts are copper powder, copper(I) chloride, copper(II) acetate, copper(II) sulphate, copper(II) oleate, copper(II) acetylacetonate, copper(II) sulphide or copper(I) oxide, and cerium(III) nitrate.

Mixtures of several of the above-mentioned catalysts can, of course, also be employed.

The amount of catalyst required is preferably in the range of from 0.01 to 10 mmol per mole of mercaptothiazole or equivalent of thiazolyl 2,2'-disulphide. It is also possible to use smaller amounts of catalyst, but this entails longer reaction times. Larger amounts of catalyst cannot be recommended for economic reasons and because of potential contamination of the reaction product.

The presence of ammonia as a component of the catalyst system is essential; in the absence of ammonia, virtually no reaction takes place (see Experiment C1). The amount of the ammonia to be employed according to the invention can be varied within wide limits. Even an amount of ammonia of as little as 0.2% by weight, based on the weight of the reaction mixture, shows an advantageous effect. An amount of 25% by weight of ammonia should not be exceeded. It is particularly advantageous to employ an amount of from 1 to 15% by weight of ammonia, based on the weight of the reaction mixture. When the amounts of ammonia are in the upper range, the speed of the reaction is particularly high, but the yield is slightly lower.

The selection of the reaction medium is highly important in the process according to the invention and depends, in particular, on the nature of the heterocyclic amine to be reacted. Very suitable media are inert organic solvents which are miscible with water, for example amides such as dimethylformamide, N-methylpyrolidone, nitriles such as acetonitriles, ethers such as glycol alkyl ethers, preferably lower alcohols, and mixtures of these solvents, or mixtures of these solvents with water. Preferred lower alcohols are straight-chain, branched or cyclic alcohols having 1 to 6 carbon atoms. If solvent/water mixtures are used, a proportion of water of up to 50% by weight based on the total weight of the reaction medium is preferred, since the yields decrease when the proportion of water is higher.

In individual cases, for example when the miscibility of the heterocyclic amine with alcohol or alcohol/water is too low, or to increase the solubility of the catalyst, it is advantageous to add to the reaction mixture a further solvent, in particular a solvent which is miscible with water. However, in general it is preferred to carry out the process without an additional solvent.

Another essential factor in the process is the reaction temperature. According to the invention, it is in the range of from 0 to 100° C. Below this range, the speed of the reaction is no longer interesting from an economic point of view, while above this range the selectivity is greatly reduced. The process according to the invention is particularly preferably carried out in the range of from 20 to 80° C.

The process according to the invention is carried out in a simple manner by injecting the oxygen or the gas containing oxygen onto the reaction mixture, or passing it into, or through, the reaction mixture, which consists of the secondary heterocyclic amine, sulphur, mercaptothiazole or dithiazolyl 2,2'-disulphide, metal catalyst, ammonia and the reaction medium.

It is also possible to add the mercaptothiazole or dithiazolyl 2,2'-disulphide and/or the secondary heterocyclic amine as well as sulphur to the reaction mixture during the reaction.

The duration of the reaction is highly dependent on the process conditions and reactants and can be several hours, but, under favorable conditions, also only a few minutes.

In most cases, the desired end product precipitates from the reaction mixture in solid form during the reaction or at the end of the reaction, after cooling, and can be filtered off. In other cases, the product is obtained by diluting the reaction mixture with water or concentrating it. Liquid products are obtained in pure form by working-up by means of distillation or extraction.

When carrying out the process according to the invention industrially, it is advantageous to recycle the mother liquor.

After the end product has been filtered off, the mother liquor can be replenished with 2-mercaptothiazole or dithiazolyl 2,2'-disulphide as well as heterocyclic amine and sulphur, and can be reemployed directly and virtually as often as desired without adversely influencing the selectivity and the yield. The process is therefore outstandingly suitable for a continuous procedure.

The process according to the invention meets essential criteria for an economical production mainly of 2-(4-morpholinodithio)benzothiazole, which is technically interesting as a vulcanization accelerator: compared with the prior art, it operates with a less expensive oxidant which is more readily accessible and can be handled with greater ease, with only virtually stoichiometric amounts of the easily accessible starting substances, the reaction rate being high and the selectivity being very high. Furthermore, no by-products are formed in the process according to the invention, following the equation of the reaction, that is to say following a different route than is the case in process of the prior art, according to which, for example, other, inorganic compounds are formed (for example chlorides or sulphates when hypochlorites or persulphates are used as oxidants), which contaminate the waste water, and require complicated disposal and which would hinder the cyclic operational procedure.

High selectivity means that the product yield corresponds mostly to the reaction rate, i.e. material losses by the formation of by-products are very low. Depending on the process conditions, the mother liquor also contains unreacted mercaptothiazole and, in some cases, also dithiazolyl disulphide. Both can be fed back into the process since both are starting compounds for the process according to the invention.

The product which can be obtained by the process according to the invention without additional purification steps is distinguished by a particularly high purity. Products are obtained which have a purity of 98% and far higher, a melting point being determined for 2-(4-morpholinodithio)benzothiazole in each case in the range between 128° and 131°. Since products according to the publication DE-A 2,238,516, quoted above, are said to have a melting point of as little as 125° to 127° even in the most favorable cases, but generally far below (compare table on page 7), the process according to the invention is also superior to the prior art process with regard to this aspect. The commercially available 2-(4-morpholinodithio)benzothiazole melts in the range of from 123° C. to 135°, and the specialized literature gives 132-134° as the melting point for ultrapure 2-(4-morphol-inodithio)benzothiazole. In view of the low melting points of products according to DE-A 2,238,516, the maximum purity of 98%, as mentioned in the table on page 7, seems too high. This publication provides no information as to which method for determining the purity was used to obtain these values; quite obviously, these values were the result of a rapid determination which also included free sulphur and 2,2'-dibenzothiazolyl disulphide. In contrast, the purity values given for the products which can be obtained according to the invention result from a determination method which definitely excludes the inclusion of the impurities mentioned (Titration by the method of J.G. Lichty; see Example 1).

Since the process according to the invention can also be carried out in the presence of water, the 2-mercaptobenzothiazole can also be added, as a starting compound, directly in the water-moist state in which it is obtained from the preparation of 2-mercaptobenzothiazole.

The present invention is illustrated in greater detail by the experimental examples below:

EXAMPLE 1

In a pressure reaction vessel equipped with a double jacket for the circulation of a heating fluid, a thermometer, a pressure gauge and a stirring device, there are placed 23.9 g of 2-mercaptobenzothiazole (143 mmol), 13.0 g of 4-morpholine (149 mmol), 4.6 g of sulphur (143 mmol), 0.1 mmol of Cu(II) acetate, 10.7 g of ammonia and 150 g of methanol. The reaction mixture is heated to 30° C and stirred vigorously, and 3 bar of oxygen are injected. Oxygen uptake is registered immediately; a clear solution is formed, and a pale beige solid subsequently precipitates. The reaction is terminated after 5 hours. The precipitate is filtered off, washed and dried.

In this way, 35.4 g of a product are obtained whose analytical data (elemental analysis, IR, $^1$H NMR, mass spectrometry) are identical to those of 2-(4-morpholinodithio)benzothiazole. The purity is 99.5% (titration by the method of J.G. Lichty, J. Applied Chem., 2, 16 (1963)), the melting point is 128-130° C. The mother liquor contains a further 3.1 g of the product, which precipitate for example when the mother liquor is concentrated to approx. 30 g and which can be filtered off. Accordingly, the overall yield of 2-(4-morpholinodithio)benzothiazole is 38.5 g (94.8% of theory).

EXAMPLE 2

The procedure is as in Example 1, but at an oxygen pressure of $4 \times 10^5$ Pa, and the solvent employed is a mixture of 120 g of methanol and 30 g of water. The reaction time is 220 minutes. The overall yield of morpholinodithiobenzothiazole is 36.5 g (87.5% of theory) at a purity of 99.0% (m.p. 129-131° C., MBT conversion 87.8%).

EXAMPLE 3

The procedure is as in Example 2, but 18.7 g of 4-morpholine (215 mmol) are employed. The reaction time is 115 minutes. The overall yield of morpholinodithiobenzothiazole is 36.1 g (88.9% of theory) at a purity of 97.4% (MBT conversion 89.6%).

EXAMPLE 4

The procedure is as in Example 2, but the reaction temperature is 50° C., and the solvent employed is a mixture of 75 g of methanol and 75 g of water. The reaction time is 90 minutes. The conversion of mercaptobenzothiazole is 90%, the yield of morpholinodithiobenzothiazole is 85.1% of theory (m.p. 128–131° C.).

EXAMPLE 5

The procedure is as in Example 2, but the reaction temperature is 50° C. and 71.5 mmol of 2,2'-dibenzothiazolyl disulphide being employed instead of 2-mercaptobenzothiazole. The reaction time is 41 minutes. The yield of mercaptobenzothiazole is 85.2% of theory at a purity of 30 98.0% (m.p. 128–130° C.).

EXAMPLE 6

The procedure is as in Example 2, but the reaction temperature is 60° C., and the solvent employed is 150 g of isopropanol. After a reaction time of 130 minutes, the yield of morpholinodithiobenzothiazole is 88.8% of theory (m.p. 129–131° C., MBT conversion 92.4%).

COMPARISON EXAMPLE 1 (C1)

The procedure is as in Example 1, but without the addition of ammonia.

After 6 hours, virtually no oxygen is taken up. When the reaction mixture is filtered, 3.75 g of sulphur are recovered in the unaltered state. The mother liquor contained unaltered mercaptobenzothiazole.

COMPARISON EXAMPLE 2 (C2)

The procedure is as in Example 6 but without the addition of sulphur. Oxygen is taken up at a considerably lower rate. After a reaction time of 3.5 hours, only morpholinothiobenzothiazole is obtained in a yield of 37.4% of theory. This example shows that the process according to the invention is based on a novel reaction principle and cannot be explained by oxidative coupling of mercaptobenzothiazole and morpholine, followed by reaction of the resulting sulphenamide with sulphur to give the disulphide.

EXAMPLE 7

23.9 g of mercaptobenzothiazole (143 mmol), 21.5 g of N-methylpiperazine (215 mmol), 4.6 g of sulphur (143 mmol), 0.1 mmol of Cu(II) acetate and 10 g of ammonia in 75 g of water and 75 g of methanol are reacted with oxygen ($3 \times 10^5$ Pa) as described in Example 1. The reaction temperature is 40° C., and the reaction time is 3.5 hours.

The pale beige solid which has formed is filtered off, washed and dried and, according to the analytical data (m.p. 108–110° C., elemental analysis, $^1$H NMR, IR), is identical to N-methyl-piperazyl-dithiobenzothiazole. The yield is 35.7 g (83.8% of theory). The mother liquor still contains 9.9% of unreacted MB and 4.4% of dibenzothiazolyl disulphide.

EXAMPLE 8

143 mmol of mercaptobenzothiazole, 149 mmol of piperidine, 143 mmol of sulphur, 0.1 mmol of Cu(II) acetate and 40 g of 25% strength aqueous ammonia solution in 120 g of methanol are reacted with oxygen ($4 \times 10^5$ Pa) as described in Example 1. The reaction temperature is 52° C., and the reaction time is 118 minutes. After the mixture has cooled to room temperature, the solid is filtered off, washed and dried. This gives 37.4 g of a pale solid whose analytical data (IR, elemental analysis, m.p. 83° C.) correspond to those of piperidinodithiobenzothiazole. The yield is 36.4 g (92.7% of theory; MBT reaction 96.1%).

EXAMPLE 9

143 mmol of MBT, 149 mmol of hexamethyleneimine, 143 mmol of sulphur, 0.5 mmol of Cu(II) acetate and 10 g of ammonia in 150 g of methanol are reacted with oxygen ($3 \times 10^5$ Pa) at 25° C. as described in Example 1. The reaction time is 150 minutes. The precipitate which has formed is filtered off, washed with methanol and dried. This gives 36.9 g (90.5% of theory) of hexamethyleneiminodithiobenzothiazole (beige-colored solid), demonstrated by elemental analysis, $^1$H NMR, IR and m.p. (65–66° C.).

EXAMPLES 10 to 13

143 mmol of mercaptobenzothiazole, 149 mmol of morpholine, 143 mmol of sulphur and 40 g of 25% strength aqueous ammonia solution in 120 g of methanol are reacted with oxygen ($4 \times 10^5$ Pa) in the presence of 0.5 mmol of various catalysts at a temperature around 50° C., in the fashion mentioned in Example 1. The particular catalyst, reaction time and product yield can be seem from the following compilation:

| Example | Catalyst | Reaction time (min) | Yield (% of theory) | MBT conversion (%) |
|---|---|---|---|---|
| 10 | CuCl | 25 | 81.3 | 84.1 |
| 11 | Cu$_2$O | 11 | 83.0 | 87.4 |
| 12 | Cu (powder) | 24 | 86.4 | 90.8 |
| 13 | Ce(NO$_3$)$_3$ | 121 | 80.8 | 84.7 |

EXAMPLE 14

The procedure is as in Example 2, but with 0.05 mmol of Cu(II) acetate and at a temperature of 50° C. The reaction time is 138 minutes, and the product yield is 82.3% of theory (m.p. 130–132° C.; MBT conversion 84.1%).

EXAMPLES 15 and 16

The procedure is as in Example 2, but with 21.4 g of ammonia (Example 15) and 5.4 g of ammonia (Example 16) at a temperature of 50° C. Furthermore, not 0.1 mmol, but 0.2 mmol of Cu(II) acetate are employed in Example 16. The reaction times are 50 minutes (Example 15) and 4 hours (Example 16), and the product yields are 81.4% (MBT conversion 84.5%, Example 15) and 86.6% of theory (MBT conversion 87.1%, Example 16).

EXAMPLE 17

The procedure is as in Example 16, but with 0.5 mmol of Cu(II) acetate and at an oxygen partial pressure of $0.6 \times 10^5$ Pa. The reaction time is 124 minutes, and the product yield is 85.1% of theory (m.p. 128–130° C.; MBT conversion 87.2%).

EXAMPLE 18

71.5 mmol of mercaptobenzothiazole, 74.5 mmol of morpholine, 71.5 mmol of sulphur, 0.25 mmol of Cu(II) acetate, 20 g of 25% strength aqueous ammonia solution in 60 g of methanol are oxidized as described in Example 1, at a temperature of 50° C., but air is employed as the oxygen-containing gas (pressure 5×10 Pa). After a reaction time of 161 minutes, morpholinodithiobenzothiazole is obtained in a yield of 84.5% of theory.

EXAMPLE 19

143 mmol of mercaptobenzothiazole, 149 mmol of morpholine, 286 mmol of sulphur (9.2 g), 0.1 mmol of copper(I) oxide and 40 g of 25% strength aqueous ammonia solution in 120 g of methanol are reacted as described in Example 1, at an oxygen pressure of $4 \times 10^5$ Pa. The reaction temperature is 52° C., and the reaction time is 43 minutes. The pale beige precipitate which has formed is filtered off, washed and dried. Based on its IR spectra, the elemental analysis and its complete solubility in alcohol, the structure of morpholino-trithiobenzothiazole is to be assigned to the product obtained. The product melts at 123 to 126° C. and has a purity of 98.5% (titration by the method of Lichty). The yield is 40.84 g (90.2% of theory).

EXAMPLE 20

The procedure is as in Example 1, but 12.5 g of 4-morpholine (143 mmol) and 10 g of ammonia are employed. The reaction time is 5 hours. The yield of morpholinodithiobenzothiazole is 37.6 g (92.4% of theory) at a purity of 99.5% (m.p. 128–130° C.). 94% of the 2-mercaptobenzothiazole is reacted. In addition, the mother liquor also contains 0.3 g of dibenzothiazyl disulphide, which can be regarded as an intermediate.

EXAMPLE 21

The procedure is as in Example 20, but 4-morpholine is employed in substoichiometric amounts (11.3 g, 130 mmol). After a reaction of time of 5.5 hours, 33.3 g of morpholinodithiobenzothiazole are obtained, corresponding to a yield of 90.1% of theory (purity 99.3%, m.p. 128–130° C., the product is completely soluble in methanol). 95.6% of the 2-mercaptobenzothiazole have reacted. In addition, the mother liquor also contains 3 g of the intermediate dibenzothiazyl disulphide.

We claim:

1. A process for the preparation of at least one compound from the group consisting of 2-aminodithiothiazoles and 2-aminotrithiothiazoles having the formula (I)

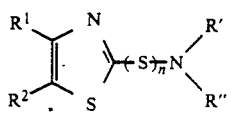

wherein:
n is essentially 2 or 3;
$R^1$ and $R^2$ may be the same or different and represent a hydrogen atom; a halogen atom; a nitro group; a hydroxyl group; an organic group wherein the organic group can optionally be monosubstituted or polysubstituted with at least one substituent selected from the group consisting of a halogen atom, a nitro group, a hydroxyl group and an alkyl or alkoxy group having 1 to 5 carbon atoms; or $R^1$ and $R^2$, taken together, represent the radical having formula (II):

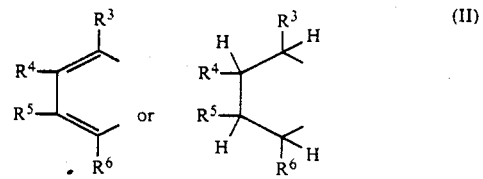

wherein $R^3$, $R^4$, $R^5$ and $R^6$ may be the same or different and are selected from the same chemical groups represented by $R^1$ and $R^2$, except the $R^3$, $R^4$, $R^5$ and $R^6$ cannot from the radical (II);
R' and R", jointly with the amine nitrogen, form an aliphatically saturated heterocyclic ring which can optionally contain at least one further hetero atom;
wherein the process comprises reacting a mixture of:
2-methcaptothiazole of the formula (III) or dithiazolyl 2,2-disulphide of the formula (IV)

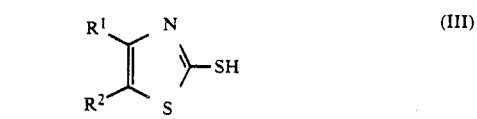

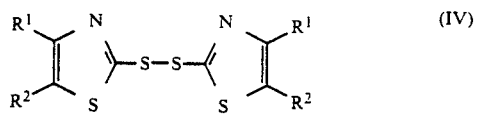

in which $R^1$ and $R^2$ are as defined above;
a saturated secondary, heterocyclic amine of the formula (V)

in which groups R' and R" are as defined above;
and sulphur;
in a reaction medium containing an inert organic solvent wherein the reaction is carried out in the presence of molecular oxygen or a gas mixture containing molecular oxygen; ammonia; and a catalyst containing copper, a copper compound or a cerium compound.

2. The process according to claim 1, wherein said organic group is an alkyl or alkoxy group having 1 to 6 carbon atoms or a cycloalkyl or aryl group having 6 to 12 carbon atoms.

3. The process according to claim 1, wherein piperazine comprises said heterocyclic ring base and the additional nitrogen atom bonds 0/50 with the 2-thiazolyldithio or 2-thiazolyltrithio groups.

4. The process according to claim 1, wherein;
$R^1$ and $R^2$ are selected from the group consisting of a chlorine or bromine atom, a hydroxyl group, a nitro group, a straight-chain or branched alkyl radical having 1–4 carbons, an alkoxy radical having 1–4 carbons and a phenyl, tolyl, ethylphenyl, nitrophenyl, chlorophenyl, bromophenyl or naphthyl radical; or
$R^1$ and $R^2$, taken together, form the group having formula (II) and substituents $R^3$ to $R^6$ are selected from the group consisting of a chlorine or bromine atom, a hydroxyl group, a nitro group, a straight-chain or branched alkyl radical having 1-4 carbons, an alkoxy radical having 1-4 carbons and a phenyl, tolyl, ethylphenyl, nitrophenyl, chlorophenyl, bromophenyl or naphthyl radical.

5. The process according to claim 4, wherein the alkyl radical is selected from the group consisting of a methyl, ethyl, propyl, isopropyl, butyl and tert-butyl radical.

6. The process according to claim 4, wherein the alkoxy radical is selected from the group consisting of a methoxy, ethoxy, propoxy and butoxy radical.

7. The process according to claim 1, wherein the secondary heterocyclic amine with formula (V) is pyrrolidine, pyrazolidine, imidazolidine, oxazolidine, thiazolidine, cyclohexa-methyleneimine, unsubstituted or substituted by alkyl groups having 1 to 4 carbon atoms, or unsubstituted or substituted piperidine, piperazine or 4-morpholine.

8. The process according to claim 1, wherein 0.9 to 2 moles of compound (V) are employed per mole of compound (III) or per equivalent of compound (IV).

9. The process according to claim 1, wherein 0.9 to 1.5 moles of compound (V) are employed per mole of compound (III) or per equivalent of compound (IV).

10. The process according to claim 1, wherein the catalyst employed is copper powder, copper(I) chloride, copper(II) acetate, copper(II) sulphate, copper(II) oleate, copper(II) acetylacetonate, copper(II) sulphide, copper(I) oxide, and/or cerium(III) nitrate.

11. The process according to claim 1, wherein the ammonia is employed in amounts of from 0.2 to 25% by weight based on the weight of the reaction mixture.

12. The process according to claim 1, wherein the ammonia is employed in amounts of from 1 to 15% by weight based on the weight of the reaction mixture.

13. The process according to claim 1, wherein the dispersion medium employed is an inert organic solvent which is miscible with water or a mixture thereof with water.

14. The process according to claim 13, wherein the reaction medium consists of saturated alcohols having 1 to 6 carbon atoms or mixtures of these solvents with water.

15. The process according to claim 14, wherein said water is present in an amount of up to 50% based on the total weight of the reaction mixture.

16. The process according to claim 1, wherein the reaction is carried out at temperatures in the range between 0 and 100° C.

17. The process according to claim 1, wherein the reaction is carried out at temperatures in the range between 20 and 80° C.

* * * * *

UNITED STATES PATENT AND TRADEMARK OFFICE
CERTIFICATE OF CORRECTION

PATENT NO. : 5,124,450

DATED : June 23, 1992

INVENTOR(S) : Manfred J. BERGFELD et al

Page 1 of 2

It is certified that error appears in the above-identified patent and that said Letters Patent is hereby corrected as shown below:

Col. 3, line 11, change "cyclic" insert --acyclic--.

Col. 4, line 52, change "a" to --as--;

line 67, after "compounds" insert --in--.

Col. 5, line 16, "1/5" to --1.5--;

line 44, change "106" to --$10^6$--.

Col. 8, line 4, change "morphol-inodithio" to --morpholinodithio--.

Col. 9, line 50, change "105" to --$10^5$--;

line 58, change "MB" to --MBT--;

line 66, change "105" to --$10^5$--.

UNITED STATES PATENT AND TRADEMARK OFFICE
CERTIFICATE OF CORRECTION

PATENT NO. : 5,124,450

DATED : June 23, 1992

INVENTOR(S) : Manfred J. BERGFELD et al

It is certified that error appears in the above-identified patent and that said Letters Patent is hereby corrected as shown below:

Claim 1, col. 12, line 18, change "2-methcaptothiazole" to --2-mercaptothiazole--.

Claim 3, col. 12, line 55, change "0/50" to --also--.

Claim 4, col. 12, line 57, change ";" to --:--.

Signed and Sealed this

First Day of February, 1994

BRUCE LEHMAN

*Attest:*

*Attesting Officer*    Commissioner of Patents and Trademarks